United States Patent
Sperl

(10) Patent No.: US 7,538,216 B2
(45) Date of Patent: *May 26, 2009

(54) GUANIDINO PHENYLALANIN COMPOUNDS USED AS UROKINASE INHIBITORS

(75) Inventor: Stefan Sperl, München (DE)

(73) Assignee: Wilex AG, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/517,518

(22) PCT Filed: Jun. 5, 2003

(86) PCT No.: PCT/EP03/05918

§ 371 (c)(1), (2), (4) Date: Jul. 1, 2005

(87) PCT Pub. No.: WO03/103644

PCT Pub. Date: Dec. 18, 2003

(65) Prior Publication Data

US 2005/0267127 A1    Dec. 1, 2005

(30) Foreign Application Priority Data

Jun. 11, 2002    (DE) ................................ 102 25 876

(51) Int. Cl.
C07D 241/04    (2006.01)
A61K 31/495    (2006.01)

(52) U.S. Cl. .................. 544/388; 514/252.12

(58) Field of Classification Search ............ 514/252.12, 514/388; 544/388
See application file for complete search history.

(56) References Cited

U.S. PATENT DOCUMENTS 6,624,169 B1    9/2003    Wilhelm et al.

2003/0013723 A1*    1/2003    Wilhelm et al. ........ 514/255.01

FOREIGN PATENT DOCUMENTS

| DE | 199 40 389 A | | 3/2001 |
|---|---|---|---|
| DE | 100 29 014 A | | 12/2001 |
| WO | WO 92/08709 | * | 5/1992 |
| WO | 0004954 A2 | | 2/2000 |
| WO | WO 00/04954 A | | 2/2000 |
| WO | WO 00/17158 | * | 3/2000 |
| WO | WO 01/70204 A | | 9/2001 |
| WO | WO 02/074756 A | | 9/2002 |

OTHER PUBLICATIONS

Sturzebecher et al., "3-Amidinophenylalanine-based inhibitors of Urokinase", Bioorganic & Medicinal Chemistry Letters, vol. 9, No. 21, Nov. 1, 1999, pp. 3147-3152.

Magdolen et al., "Natural and synthetic inhibitors of the tumor-associated serine protease urokinase-type plasminogen activator", Advances in Experimental Medicine and Biology, vol. 477, 2000, pp. 331-341.

Heechung et al., "Selective Inhibition of Urokinase by Substituted Phenylguanidines: . . . ", Journal of Medicinal Chemistry, American Chemical Society, vol. 33, No. 11, 1990, pp. 2956-2961.

Sperl et al., "(4-Aminomethyl)phenylguanidine derivatives as nonpeptidic highly selective inhibitors of human urokinase", Proceedings of the National Academy of Sciences, vol. 97, No. 10, May 9, 2000, pp. 5113-5118.

Nienaber et al., "Re-engineering of human urokinase provides a system for structure-based drug design at high resolution and reveals a novel structural subsite", Journal of Biological Chemistry, vol. 275, No. 10, Mar. 10, 2000, pp. 7239-7248.

Product Catalogue, *Pefachrome®-Series: Chromogenic and fluorogenic peptide substrates*, Pentapharm Ltd., pp. 1-39.

Product Catalogue 1998, *Pefachrome ®-Series: Chromogenic and fluorogenic peptide substrates*, Pentapharm Ltd., pp. 1-47.

* cited by examiner

*Primary Examiner*—Shailendra Kumar
(74) *Attorney, Agent, or Firm*—Rothwell, Figg, Ernst & Manbeck

(57) ABSTRACT

The invention relates to the use of derivatives of 3-guanidinophenylalanine as urokinase inhibitors for treating malignant tumors and metastasis.

15 Claims, 2 Drawing Sheets

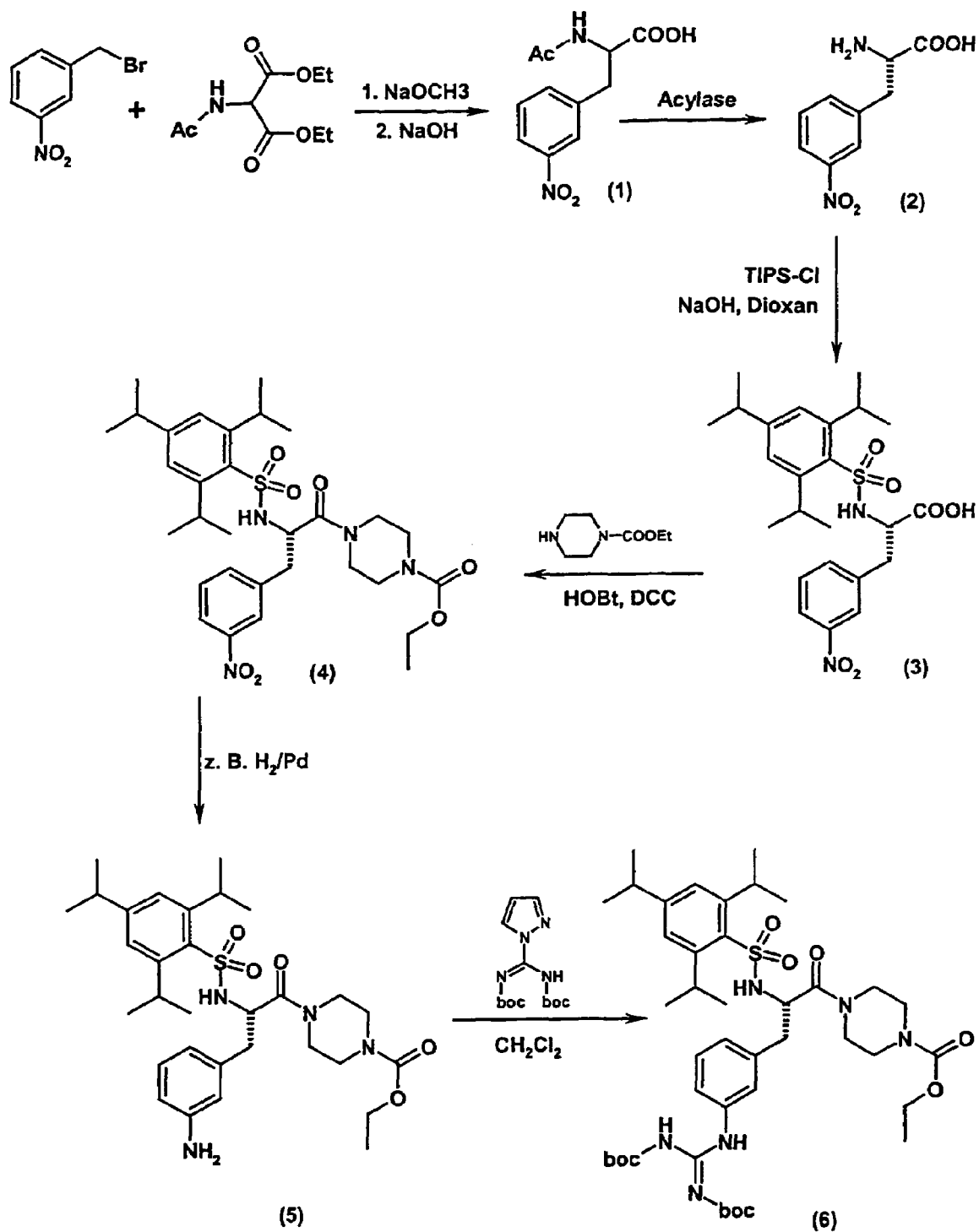

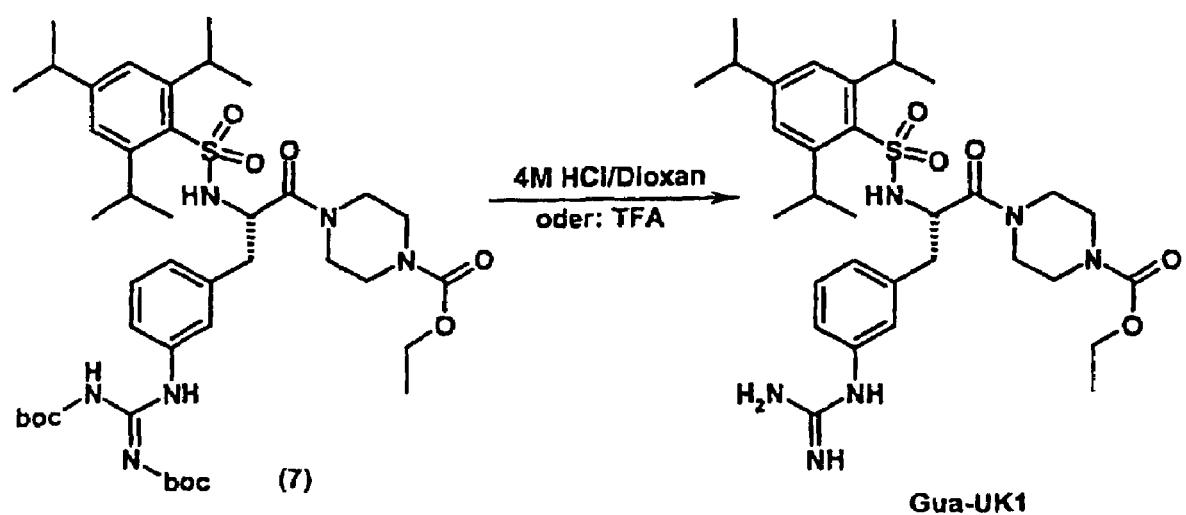
CONTINUED

GUANIDINO PHENYLALANIN COMPOUNDS USED AS UROKINASE INHIBITORS

CROSS REFERENCE TO RELATED APPLICATION

This application is a 35 USC § 371 National Phase Entry Application from PCT/EP03/05918, filed Jun. 5, 2003, and designating the United States.

The invention relates to the use of derivatives of 3-guanidinophenylalanine as urokinase inhibitors, in particular for treating malignant tumors and metastases or as agents for targeting lymph cells, and for treating diseases of the lymphatic tissue, in particular lymphomas.

The ability of solid tumors to spread into, and metastasize in, surrounding tissue correlates with the breakdown or remodeling of the extracellular matrix (tumor stroma) in the environment of the tumor cell or with its ability to penetrate the basement membrane. Although the (patho)biochemical circumstances have not yet been finally clarified, the plasminogen activator urokinase (uPA) and the urokinase receptor (uPAR) are considered to be of central importance. uPA mediates the proteolytic cleavage of plasminogen to give plasmin. Plasmin is in turn a protease which has a broad spectrum of activity and is able to directly break down the components of the extracellular matrix such as fibrin, fibronectin, laminin and the protein backbone of the proteoglycans. In addition, plasmin is able to activate "latent" metalloproteases and the inactive proenzyme of uPA, i.e. prb-uPA.

Tumor cells and nonmalignant cells of the tumor stroma synthesize and secrete the enzymically inactive proenzyme pro-uPA. Proteases, such as plasmin or the cathepsins B and L, cleave pro-uPA, by means of limited proteolysis, to give the active serine protease HMW-uPA (HMW=high molecular weight). pro-uPA and the active protease HMW-uPA bind to the cell surface receptor uPAR (CD87). Plasmin(ogen) also binds to specific receptors on the plasma membrane of the tumor cell, thereby focussing and amplifying plasminogen activation in the direct environment of the tumor cell. Invasive cells are consequently provided with the possibility of breaking down the extracellular matrix without withdrawing, by proteolysis, from the substrate which is required for directional movement.

A variety of cell-biological studies have shown that the cell-associated plasminogen activator system is of special importance in the cascade-like reaction pathways of tumor-associated proteolysis systems (Wilhelm et al. (1994) The Urokinase/Urokinase receptor system: A new target for cancer therapy? In: Schmitt M., Graeff H., Kindermann G. (ed.): Prospects in Diagnosis and Treatment of Cancer. International Congress Series, Excerpta Medica 1050, Amsterdam, Elsevier 1994, pp 145-156). It has been observed that the ability of cultures of human colon carcinoma cells to migrate through an extracellular matrix depends on the degree to which the uPA receptors are saturated with active uPA (Hollas et al., Cancer Res. 51 (1991), 3690-369.5). It has also been observed, in a cell culture model, that the invasive potential of cells is reduced if the proteolytic activity of uPA is inhibited by PAI-1 (Cajot et al., Proc. Natl. Acad. Sci. USA 87 (1990), 6939-6943) or PAI-2 (Baker et al., Cancer Res. 50 (1990), 467.6-4684). A comparable effect has been achieved by inhibiting the binding of uPA to the cell surface by blocking the receptor with proteolytically inactive uPA variants (Cohen et al., Blood 78 (1991), 479-487; Kobayashi et al.,. Br. J. Cancer 67 (1993), 537-544). Transfecting epidermoid carcinoma cells with a plasmid which was expressing an antisense transcript directed against a part of uPAR also resulted, by suppression of uPAR synthesis, in a decrease in the invasiveness of these cells (Kook, EMBO J. 13 (1994), 3983-3991). Antibodies directed against uPA and PAI-1 reduced the invasive potential of lung cancer cells in vitro (Liu et al., Int. J. Cancer 60 (1995), 501-506). It has also been possible to confirm the influence of the plasminogen activatory system on the metastasis process in animal tumor models. Thus, the formation of lung metastases by human carcinoma cells in chick embryos was almost completely prevented by adding antibodies directed against uPA (Ossowski and Reich, Cell 35 (1983), 611-619). Metastasizing human carcinoma cells have been transfected with an expression plasmid which encoded a proteolytically. Inactive, but uPAR-binding, uPA mutant. It was found in a mouse model that, following injection, the carcinoma cells which were synthesizing inactive uPA formed a significantly lower number of metastases than did the untransfected cells (Crowley et al., Proc. Natl. Acad. Sci. USA 90 (1993) 5021-5025). In addition, inhibition of the intraperitoneal dissemination of human ovarian carcinoma cells was observed in nude mice following the administration of uPA antisense oligonucleotides (Wilhelm et al., Clin. Exp. Metast. 13 (1995), 296-302).

In recent years, the clinical relevance of factors of the plasminogen activator system (uPA, uPAR, PAI-1 and PAI-2) for the prognosis of patients having solid malignant tumors has been investigated intensively. In this connection, it has been found that the content of uPA antigen in a variety of tumors (e.g. breast, ovary, stomach, lung, kidney, etc.) is a strong prognosis factor both for relapse-free survival and for mortality (see, for example, Schmitt et al., J. Obstet. Gynaecol. 21 (1995), 151-165; Jaenicke et al., Breast Cancer Res. Treat. 24 (1993), 195-208; Kuhn et al., Gynecol. Oncol. 55 (1994), 401-409; Nekarda et al., Lancet 343 (1994), 117; Pedersen et al., Cancer Res. 54 (1994), 4671-4675). Elevated concentrations of uPAR in lung (Pedersen et al., see above) and breast cancer tissue (Duggan et al., Int. J. Cancer 61 (1995), 597-600; Ronne et al., Breast Cancer Res. Treat. 33 (1995), 199-207), as well as in stomach cancer, both in the tumor tissue itself (Heiss et al., J. Clin. Oncol. 13 (1995), 2084-2093) and in the tumor cells which have disseminated into the bone marrow (Heiss et al., Nature Medicine 1 (1995), 1035-1039), likewise correlate with an unfavorable prognosis.

The use of synthetic uPA inhibitors offers the possibility of suppressing the invasion and dissemination of tumor cells. However, the development of specific uPA inhibitors is a difficult matter since the tissue-type plasminogen activator (tPA) has an identical specificity for cleaving the Arg560/Val561 peptide bond of plasminogen. In most cases, therefore, low molecular weight uPA inhibitors also inhibit tPA and, as a consequence, also inhibit tPA-mediated fibrinolysis. In addition, care must be taken to ensure that synthetic uPA inhibitors do not exhibit any strong inhibition of plasmin.

Despite these limitations, some inhibitors are known which possess a certain degree of specificity toward uPA but which have low inhibitory capacity, such as benzamidine and β-naphthamidine derivatives, with the most active compound inhibiting uPA with a $K_i$=2.2 µmol/l (Stürzebecher and Markwardt, Pharmazie 33 (1978), 559), or amiloride, with a $K_i$=7 µmol/l (Vassalli and Belin, FEBS. Lett. 214 (1987), 187-191).

DE-A-30 35 086 discloses cyclohexanecarboxylic acid derivatives which have inhibitory effects on proteases such as trypsin, chymotrypsin, thrombin and uPA. However, the investigated compounds only exhibit quite low, and furthermore nonspecific, inhibition of uPA. EP-A-0 183 271 discloses lysine derivatives and their use as protease inhibitors. This document also describes a benzamidinolysine derivative (compound 108) which inhibits uPA in vitro but also has a comparable effect on other proteases such as trypsin or plasma kallikrein. WO 95/17885 discloses low molecular weight polypeptides as being uPA inhibitors.

4-Substituted benzothiophene-2-carboxamidines, having a $K_i=0.16$ µmmol/l in the case of benzothiophene-623, constitute another class of known uPA inhibitors (Towle et al., Cancer Res. 53 (1993), 2553-2559). These inhibitors have a significantly higher affinity for uPA than for tPA and plasmin. uPAR-bound uPA is also inhibited with higher efficiency. However, a disadvantage of these substances is that it is a complicated matter to synthesize them chemically and that few possibilities for modifying the structure are available or have thus far been demonstrated.

Nα-Arylsulfonyl- and Nα-Arylsulfonylaminoacyl derivatives of 3-amidinophenylalanine are known to be selective inhibitors of thrombin (Markwardt et al., Thromb. Res. 17 (1980), 425-431) and, respectively, coagulation factor Xa (Stürzebecher et al., Thromb. Res. 54 (1989), 245-252). WO 92/08709 and WO 96/05189 also disclose the use of amidinophenylalanine derivatives as inhibitors of blood coagulation, in particular as inhibitors of thrombin. WO 94/18185 discloses amidino and guanidino derivatives of phenylalanine and their use as inhibitors of blood coagulation, in particular as substances which have an antithrombotic effect.

Piperidides and piperazides of 3-amidinophenylalanine, among which indicative structures for inhibiting fibrinolytic enzymes were also found, have been investigated intensively (Stürzebecher et al., J. Enzyme Inhibition 9, 87-99, 1995; Stürzebecher et al., J. Med. Chem. 40, 3091-3099, 1997). While Stürzebecher et al. (1995) only describe the inhibition of thrombin, factor Xa, plasmin and trypsin, Stürzebecher et al. (1997) also contain information with regard to the inhibition of uPA. In the case of Nα-2-naphthylsulfonyl-, Nα-2-(2, 2,5,7,8-pentamethylchroman-6-yl)sulfonyl- and Nα-2-camphor-10-ylsulfonyl-substituted 3-amidinophenylalaninepiperazides, a $K_i$ value of from 28 to 140 µmol/l was found for uPA, with this $K_i$ value being about three orders of size higher than the inhibition constant for thrombin.

It has also been found that 3-amidinophenylalanine derivatives which are substituted by a phenyl radical at position 2 are selective inhibitors of uPA which are active in vivo (PCT/EP99/05145). In addition, it has been found that these substances exhibit a high degree of selectivity for lymphatic tissue and are therefore suitable for the use as agents for targeting lymph cells, for example for treating malignant diseases of the lymphatic tissue, such as lymphomas.

However, there is still a need to develop additional inhibitors which have a high degree of selectivity for uPA in order to further clarify the role which uPA and uPAR play in various diseases, especially in connection with tumor dissemination and metastasis.

Surprisingly, it has now been found that replacing the amidino function with the guanidino function in the phenylalanine derivatives does not have a detrimental influence on the inhibitory effect in regard to uPA and that, furthermore, such inhibitors exhibit a high degree of selectivity for uPA.

The present invention relates to novel 3-guanidino-phenylalanine-derived urokinase inhibitors of the formula I,

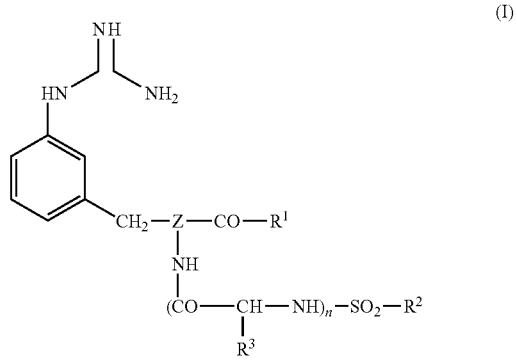

which are present as racemates and as L- or D-configured compounds and in which

R1 (a) is OH or $OR^4$, where $R^4$ is an optionally, e.g. by hydroxyl, carboxyl, sulfonyl, nitro, cyano, oxo and/or halogen, substituted, branched or unbranched $C_1$-$C_8$-alkyl, $C_3$-$C_8$-cycloalkyl or aralkyl, e.g. benzyl or phenylethyl, (b) is a group of the formula

in which $R^5$ and $R^6$ are arbitrary radicals which are compatible with the overall structure, where, in particular, (i) $R^5$ and $R^6$ are H,
(ii) $R^5$ is H and $R^6$ is an optionally, e.g. by hydroxyl, carboxyl, sulfonyl, nitro, cyano, oxo and/or halogen, substituted, branched or unbranched $C_1$-$C_8$-alkyl, aralkyl, e.g. benzyl or phenylethyl, or $C_5$-$C_8$-cycloalkyl,
(iii) $R^5$ and $R^6$ are in each case, independently, an optionally, e.g. by hydroxyl and/or halogen, substituted, unbranched or branched $C_1$-$C_4$-alkyl, or
(iv) $R^5$ is H and $R^6$ is —$NH_2$ or an amino group which is, in particular, substituted by aryl or heteroaryl,
(v) $R^5$ is H or an optionally, e.g. by hydroxyl and/or halogen, substituted, unbranched or branched $C_1$-$C_4$-alkyl and $R^6$ is the radical of an amino acid, e.g. of an α-, β- or ω-aminocarboxylic or aminosulfonic acid, or the radical of a peptide e.g. having a length of up to 50 amino acids or of a polypeptide e.g. having a length of more than 50 amino acids up to 1000 amino acids, (c) is a group of the formula

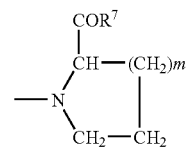

in which m denotes the number 1 or 2 and in which one or more of the methylene groups is/are optionally, e.g. by a hydroxyl, carboxyl, $C_1$-$C_4$-alkyl or aralkyl radical, e.g. benzyl or phenylethyl, substituted, where the group (c) is racemic or D- or L-configured, and $R^7$ has the meaning of $R^1$ in subsections (a), (b) and (f), (d) is a group of the formula

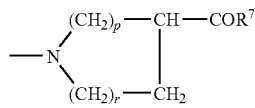

in which p=r=1, p=1 and r=2 or p=2 and r=1 and in which one or more of the methylene groups is/are optionally, e.g. by a hydroxyl, carboxyl, $C_1$-$C_4$-alkyl or aralkyl radical, e.g. benzyl or phenylethyl, substituted, and $R^7$ has the meaning of $R^1$ in subsections (a), (b) and (f), (e) is a piperidyl group which is optionally substituted, e.g. by a $C_1$-$C_4$-alkyl, $c_1$-$C_3$-alkoxy or hydroxyl radical, in one of the positions 2, 3 and 4, where an additional aromatic or cycloaliphatic ring, preferably phenyl or cyclohexyl, is optionally fused, in the 2,3 or 3,4 position, based on the heteroatom, to the heterocycloaliphatic rings of the formulae (c), (d) and (e), (f) is a group of the formula

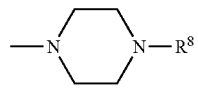

in which $R^8$ (i) is an optionally, e.g. by $C_1$-$C_6$-alkyl, $C_1$-$C_3$-alkoxy, hydroxyl, carboxyl, sulfonyl, nitro, cyano, oxo and/or halogen, substituted $C_1$-$C_6$-alkyl or aryl radical, such as phenyl, p-halophenyl or naphthyl, (ii) is a saturated or unsaturated, branched or unbranched $C_1$-$C_6$-alkoxy radical, (iii) is an oxycarbonyl radical —COOR', in which R' is H or a group such as $C_1$-$C_6$-alkyl, aryl or aralkyl which is optionally substituted by $C_1$-$C_3$-alkoxy, hydroxyl, carboxyl, sulfonyl, nitro, cyano, oxo and/or halogen, e.g. an ethoxycarbonyl, phenoxycarbonyl or benzyloxycarbonyl radical, or (iv) is an aminocarbonyl radical —CONR'R", in which R' and R" are in each case, independently, H or a group such as $C_1C_4$-alkyl, aryl or aralkyl which is optionally substituted by $C_1$-$C_3$-alkoxy, hydroxyl, carboxyl, sulfonyl, nitro, cyano, oxo and/or halogen, e.g. ethylaminocarbonyl, (g) is an acyl radical of the formula —COX, where X is (i) H, an optionally, e.g. by hydroxyl, carboxyl, sulfonyl, nitro, cyano, oxo and/or halogen, substituted, unbranched or branched alkyl radical, preferably a $C_1$-$C_6$-alkyl radical, in particular methyl, (ii) an optionally, e.g. by $C_1$-$C_6$-alkyl, $C_1$-$C_3$-alkoxy, hydroxyl, carboxyl, sulfonyl, nitro, cyano, oxo and/or halogen, substituted aryl or heteroaryl radical such as phenyl, p-halophenyl or thienyl, or (iii) an optionally, e.g. by hydroxyl, carboxyl, sulfonyl, nitro, cyano, oxo and/or halogen, substituted cycloalkyl radical, preferably a $C_3$-$C_{10}$-cycloalkyl radical, (h) is an aralkyl radical, e.g. benzyl or phenylethyl, in which the aromatic radical is optionally substituted, e.g. by a halogen atom or by a $C_1$-$C_6$-alkyl, $C_1$-$C_3$-alkoxy, hydroxyl, cyano, carboxyl, sulfonyl or nitro group, (i) is a carboxamide radical of the formula —CONR'R", a thiocarboxamide radical —CSNR'R" or an acetamide radical —$CH_2$—CONR'R", where (i) R' and R" are H, (ii) R' and R" are in each case, independently, $C_1$-$C_4$-alkyl, (iii) R' is H and R" is $C_1$-$C_4$-alkyl, (iv) R' is H and R" is aryl, e.g. phenyl, or (v) R' and R" form, together with the nitrogen atom, a heterocycloaliphatic ring having 5-7 ring members which can carry an additional heteroatom, e.g. N, O and/or S, (j) is an $SO_2$—Y radical in which Y (i) is an optionally, e.g. by hydroxyl, carboxyl, sulfonyl, nitro, cyano, oxo and/or halogen, substituted $C_1$-$C_8$-alkyl, preferably methyl, trifluoromethyl or trichloromethyl, (ii) is an optionally, e.g. by $C_1$-$C_6$-alkyl, $C_1$-$C_3$-alkoxy, hydroxyl, carboxyl, sulfonyl, nitro, cyano, oxo and/or halogen, substituted aryl or heteroaryl, such as phenyl, 4-methylphenyl, 2,4,6-trimethylphenyl, 2,4,6-triisopropyl-phenyl, 4-methoxy-2,3,6-trimethylphenyl, 2,2-dimethyl-6-methoxychromanyl, 2,2,5,7,8-pentamethylchromanyl, anthra-quinonyl, naphthyl or quinolyl, or O-aryl, preferably O-phenyl, or O-heteroaryl, or (iii) is —NR'R", where R' and R" are in each case, independently, H or $C_1$-$C_3$-alkyl, (k) is a cycloaliphatic ring having 5 to 8 C atoms which is optionally substituted, e.g. by a $C_1$-$C_6$-alkyl, $C_1$-$C_3$-alkoxy, halogen, hydroxyl and/or oxo group, (l) is an optionally, e.g. by $C_1$-$C_6$-alkyl, $C_1$-$C_3$-alkoxy, hydroxyl, carboxyl, sulfonyl, nitro, cyano, oxo and/or halogen, substituted heteroaryl radical, such as pyridyl or pyrimidyl, or heterocycloaliphatic radical, for example N-methylpiperidyl, (m) is a functionalized alkyl radical of the formula —$(CH_2)_n$-X, where the alkyl chain is unbranched or branched, n=1 to 8 and the functional radical X (i) is a hydroxyl group whose H atom is optionally substituted by a $C_1$-$C_4$-alkyl group, aralkyl group, e.g. benzyl or phenylethyl, aryl group, e.g. phenyl, $C_1$-$C_4$-hydroxyalkyl group or acyl group. CO-alkyl, ($C_1$-$C_6$), (ii) is a halogen atom, (iii) is a tertiary amino group of the formula —$N(Alk)_2$, where the alkyl groups have 1 to 3 C atoms and also preferably the same meaning, and the nitrogen atom optionally belongs to a heterocyclo-aliphatic ring which has 5-7 ring members and can carry an additional heteroatom, e.g. N, O and/or S, $R^2$ is an optionally, e.g. by $C_1$-$C_6$-alkyl, $C_1$-$C_3$-alkoxy, hydroxyl, carboxyl, sulfonyl, nitro, cyano, oxo and/or halogen, substituted phenyl radical, such as phenyl, 4-methylphenyl, 2,4,6-trimethylphenyl, 2,4,6-triisopropylphenyl or 4-methoxy-2,3,6-trimethylphenyl, $R^3$ is H or branched or unbranched $C_1$-$C_4$-alkyl and n is 0 or 1, Z is N or $CR^9$, where $R^9$ is H or branched or unbranched $C_1$-$C_4$-alkyl.

The compounds can also be present as salts, preferably as physiologically tolerated acid salts, e.g. as salts of mineral acids, particularly as hydrochlorides, or as salts of suitable organic acids.

Of the compounds which are defined in the general claims, those in which $R^1$ corresponds to a group of the formulae (b), (d) and (f), $R^2$ is a singly, doubly or triply alkyl-substituted phenyl radical, in particular a 2,4,6-substituted phenyl radical, e.g. a 2,4,6-triisopropylphenyl radical, and n=0, are of particular importance. Preference is furthermore given to compounds in which Z is CH or N. $R^1$ is particularly preferably a 4-ethoxycarbonyl piperazide radical or a 4-ethylaminocarbanyl piperazide radical.

The present invention relates to the compounds of formula (I) as such, as active compounds in pharmaceutical compositions and for use for preventing or treating diseases which are associated with urokinase and/or urokinase receptor, in particular with their overexpression.

The compounds of the formula I can be prepared, and tested for their in-vitro biological activity, in what is in principle a known manner, as described, for example, in WO 92/08709 and WO 94/18185.

(L)-, (D)- or (D,L)-3-nitrophenylalanine is reacted with an appropriate sulfonyl chloride or a sulfonylated amino acid or its halide in the presence of a base to give a compound of the formula I which possesses a nitro function and in which. $R^1$=OH and $R^2$ and $R^3$ and n correspond to the meanings defined in the general claims. The resulting compounds are converted, by means of esterification with an appropriate alcohol under acid-catalytic conditions, into compounds of the formula I where $R^1$=(a). Using a method which is customary in peptide chemistry, e.g. a DCC method in the presence of HOBt, the compounds of the formula I possessing a corresponding $R^1$ can be prepared by reacting the carboxylic acids of the formula I ($R^1$=—OH) with a nucleophile of the structures (b), (e) and (f). For synthesizing compounds in which $R^1$=(c) and (d), the carboxylic acids of the formula I in which $R^1$=OH are initially reacted with cycloaliphatic amino acid esters of the structures (c) and (d), where $R^7$ is preferably —$OCH_3$ and, respectively, —$OC_2H_5$, and the resulting carboxylic esters are hydrolyzed under mild acidic or alkaline conditions to give the corresponding carboxylic acids which can subsequently be esterified in already described manner or reacted with nucleophiles of the structure (b), (e) or (f), with compounds of the formula I in which $R^1$=(c) and (d) and $R^7$=(a), (b), (e) and (f) being obtained.

Target compounds of the formula I containing a guanidine structure can be obtained from the nitro compounds in a known manner, with the corresponding amines as a rule initially being obtained by reduction of the nitro group, and with the amines then being converted, by reaction with a suitable guanidinylating reagent, such as guanylpyrazole, into the guanidino compounds.

Urokinase inhibitors according to the invention can be used, where appropriate together with at least one suitable pharmaceutical auxiliary or carrier substance, for producing drugs, e.g. drugs which can be administered orally, subcutaneously or intravenously, for controlling tumors or in diagnosis. It is likewise possible to administer them in combination with other active compounds, e.g. other urokinase inhibitors such as antibodies and/or peptides.

The drugs for controlling tumors in humans and animals can be administered topically, orally, rectally or parenterally, e.g. subcutaneously or intravenously, in the form of tablets, sugar-coated tablets, capsules, pellets, suppositories, solutions or transdermal systems such as plasters.

The compounds of the formula (I) are particularly preferably Nα-(2,4,6-triisopropylphenylsulfonyl)-3-guanidino-(D,L)-phenylalanine-4-ethoxycarbonyl piperazide and Nα-(2,4,6-triisopropylphenylsulfonyl)-3-guanidino-(D,L)-phenylalanine-4-ethylaminopiperazide or the L-enantiomers thereof or pharmaceutically tolerated salts of these compounds, e.g. the hydrochlorides. These substances have good solubility behavior.

The compounds according to the invention are able to inhibit the growth and/or dissemination of malignant tumors, e.g. tumor dissemination in association with pancreatic carcinoma, tumor growth of the mammary carcinoma and the metastasis of tumors, in a highly efficient manner. In this connection, the uPA inhibitors can, where appropriate, be employed together with other antitumor agents or with other types of treatment, e.g. irradiation or surgical interventions. In addition, the inhibitors according to the invention are also active in the case of other uPA- and/or uPAR-associated diseases (e.g. for example in preventing blister formation in connection with the skin disease pemphigus vulgaris).

uPA inhibitors according to the invention are preferably characterized by the fact that they possess a $K_i$ value for uPA which is at least 2 times, preferably at least 5 times and particularly preferably at least 10 times lower than that for plasmin, thrombin and/or tPA. It is therefore remarkable that the compounds according to the invention only have a slight influence on blood coagulation and consequently exhibit a surprising degree of selectivity.

The substances according to the invention of the formula I can be employed in the form of conjugates with physiologically active substances, e.g. together with radiolabels or with cytotoxic agents, e.g. chemotherapeutic agents, such as cisplatin, carboplatin, 5-fluorouracil, doxorubicin, epirubicin or taxol, or peptides. Furthermore, the substances can also be incorporated into the membranes of carrier vesicles, e.g. liposomes, and consequently enable active substances, e.g. cytotoxic agents such as doxorubicin, which are enclosed in the carrier vesicles to be targeted.

The following example and figure are intended to clarify the invention.

FIG. 1 shows a scheme for synthesizing the substance Nα-(2,4,6-triisopropylphenylsulfonyl)-3-guanidino-(L)-phenylalanine-4-ethoxycarbonylpiperazine, which is preferred in accordance with the invention.

EXAMPLE 1

Synthesizing Nα-2,4,6-triisopropylphenylsulfonyl-3-guanidino-(L)-phenylalanine-4-ethoxycarbonylpiperazine hydrochloride 1.1 N-Acetyl-(D/L)-(3-nitrophenylalanine)

A solution of 3-nitrobenzyl bromide (7.5 g; 35.7 mmol), diethyl acetamidomalonate (7.54 g; 35.7 mmol) and potassium iodide (0.3 g, 1.79 mmol) in abs. dioxane is stirred at 80° C. under argon while a solution of sodium ethanolate (25 ml, 37.5 mmol) is added dropwise over a period of 1.5 h. The reaction mixture is refluxed for 2 h and stirred overnight at RT. After 3M NaOH (24 ml) has been added at 80° C., the mixture is stirred at 95° C. for a further 4 h. The dioxane is distilled off and the aqueous phase is extracted 3× with ethyl acetate (30 ml). The aqueous phase is then acidified to pH 1 with 1M HCl and extracted 3× with ethyl acetate (30 ml). The product crystallizes out when the last 3 pooled ethyl acetate phases are slowly evaporated. It is filtered off and dried in vacuo.

Yield: 6 g (69%), ESI-MS: m/z: 253.3 (M+H)$^+$; calculated for $C_{11}H_{12}N_2O_5$: 252.2

1.2 (L)-(3-Nitrophenylalanine)

A solution of N-acetyl-(D/L)-(3-nitrophenylalanine) (1.1) (5.75 g; 22.8 mmol) in 350 ml of water is adjusted to pH 7.5 with 1M NaOH. After Amano Acylase (0.25 g) has been added, the mixture is stirred slowly at 37-38° C. for 6 days. It is then acidified to pH 3 with 1M HCl and extracted 3× with ethyl acetate (in each case 100 ml); the organic phase is discarded. The pH of the aqueous solution is adjusted to 6.8 with 1 M NaOH, after which the water is distilled off gradually and the product, which has precipitated, is filtered off and dried.

Yield: 1.7 g (35%), ESI-MS: m/z: 211.3 (M+H)$^+$; calculated for $C_9H_{10}N_2O_4$: 210.2

1.3 N-Triisopropylphenylsulfonyl-(L)-(3-nitrophenyl-alanine)

1 M NaOH (8 ml) and a solution of triisopropylphenyl-sulfonyl chloride (2.42 g; 7.99 mmol) in dioxane (15 ml) are added dropwise in parallel, over a period of 1.5 h, to a solution of (L)-(3-nitrophenylalanine) (1.2) (1.7 g; 8.09 mmol) in a mixture of 1 M NaOH (8 ml) and dioxane (15 ml). The reaction mixture is then stirred at RT overnight. After the solvent has been stripped off, the residue is taken up in ethyl acetate (50 ml) and this solution is washed 3× with a 5% solution of $KHSO_4$ (in each case 25 ml) and 3× with water (in each case 20 ml). After the solvent has been stripped off, the product is dried under high vacuum.

Yield: 3.52 g (92%), HPLC purity, approx. 80%; ESI-MS: m/z: 477.7 (M+H)$^+$; calculated for $C_{24}H_{32}N_2O_6S_1$: 476.6

1.4 N-Triisopropylphenylsulfonyl-(L)-(3-nitrophenyl-alanine)-4-ethyloxycarbonyl piperazide A solution of N-triisopropylphenylsulfonyl-(L)-(3-nitrophenylalanine) (1.3) (3.52 g; 7.39 mmol) 1-ethyloxycarbonylpiperazine (1.19 g; 7.47 mmol) and HOBt (1.53 g; 11.3 mmol) in absolute DMF (15 ml) is cooled down to 0° C. and a solution of DCC (1.7 g; 3.91 mmol) in DMF (10 ml) is added dropwise. The reaction mixture is stirred at RT for 18 h. After the solvent has been evaporated in vacuo down to approx. 7 ml, the residue is diluted with ethyl acetate (50 ml) and this mixture is washed 3× with a 5% solution of $KHSO_4$ and 3× with water. After the solvent has been stripped off, the crude product is purified by flash chromatography through a silica gel column (gradient: petroleum ether:methyl tert-butyl ether (MTBE) 1:1 to MTBE:ethyl acetate 1:1).

Yield: 1.45 g (32%), ESI-MS: m/z: 617.9 (M+H)$^+$; calculated for $C_{31}H_{44}N_4O_7S_1$: 616.8

1.5 N-Triisopropylphenylsulfonyl-(L)-(3-aminophenyl-alanine)-4-ethyloxycarbonyl piperazide A solution of N-triisopropylphenylsulfonyl-(L)-(3-nitrophenylalanine)-4-ethyloxycarbonyl piperazide (1.4) (1.4 g; 2.27 mmol) in ethanol is hydrogenated, at RT for 8 h, over 0.15 g of 10% Pd on active charcoal. After the catalyst has been filtered off, the solvent is stripped off in vacuo and the product is dried in +vacuo.

Yield: 1.35 g (98%), ESI-MS: m/z: 587.9 (M+H)$^+$; calculated for $C_{31}H_{46}N_4O_5S_1$: 586.8

1.6 N-Triisopropylphenylsulfonyl-(L)-(3-(N'N"bis-BOC-guanidino)phenylalanine)-4-ethyloxycarbonyl piperazide A solution of N-triisopropylphenylsulfonyl-(L)-(3-aminophenylalanine)-4-ethyloxycarbonyl piperazide (1.5) (0.5 g; 0.85 mmol) and N,N'-di-BOC-guanylpyrazole (0.27 g; 0.85 mmol) in methylene chloride (10 ml) is stirred at RT for 6 d under argon. After the solvent has been stripped off, the residue is taken up in ethyl acetate and this solution is extracted 3× with a 5% solution of $KHSO_4$ and 3× with a 5%-solution of $NaHCO_3$ (in each case 15 ml). After the solvent has been stripped off, the crude product is purified chromatographically through a silica gel column (gradient: petroleum ether (PE)/ethyl acetate (EA) 4:1 to PE/EA 7:3).

Yield: 0.6 g (85%), ESI-MS: m/z: 829.9 (M+H)$^+$; calculated for $C_{42}H_{64}N_6O_9S_1$: 829.1

1.7 N-Triisopropylphenylsulfonyl-(L)-(3-guanidino-phenylalanine)-4-ethyloxycarbonyl piperazide N-Triisopropylphenylsulfonyl-(L)-(3-(N'N"bis-BOC-guanidino)phenylalanine)-4-ethyloxycarbonyl piperazide (1.6) (0.5 g; 0.603 mmol) is deprotected by stirring in 4 M HCl in dioxane (8 ml). The solvent is stripped off and the residue is taken up in a little methanol; this solution is poured into MTBE (35 ml), in connection with which the product precipitates out and is subsequently filtered off and dried in vacuo.

Yield: 0.18 g (49%), ESI-MS: m/z: 629.5 (M+H)$^+$; calculated for $C_{32}H_{48}N_6O_5S_1$: 628.8; HPLC: $t_R$=6.8 min The compounds were characterized mass spectrometrically using a Waters' ZQ 2000 ESI-MS mass spectrometer (Waters GmbH, Eschborn, Germany); a purity test was carried out by means of HPLC using an X-Terra C8 column, 150×2.1 mm Ø (Waters GmbH, Eschborn, Germany), gradient: water/methanol 50:50 to 5:95 in 15 min.

EXAMPLE 2

Synthesizing Nα-2,4,6-triisopropylphenylsulfonyl-3-guanidino-(L)-phenylalanine-4-ethylaminocarbon-ylpiper-azine hydrochloride The synthesis was effected in analogy with that described in Example 1 apart from the fact that 1-ethylaminocarbon-ylpiperazine was used in place of 1-ethyloxycarbonylpipera-zine.

EXAMPLE 3

In-vitro inhibition of urokinase by selected compounds of the formula I

| Configuration | $R^1$ | $R^2$ | n | $K_i$ μmol/l |
|---|---|---|---|---|
| L | —N⟨  ⟩N— | COOC$_2$H$_5$ | TIPP  0 | 0.47 |

Abbreviations: TIPP - 2,4,6-triisoprophylphenyl

Determining the Inhibitory Effect

In order to determine the activity of the inhibitor, 200 μl of Tris buffer (0.05 mol/l, containing the inhibitor, 0.154 mol of NaCl/l, 5% ethanol, pH 8.0), 25 μl of substrate (Pefachrome UK or Bz-βAla-Gly-Arg-pNA in H$_2$O; Pentapharm Ltd., Basle, Switzerland) and 50 μl of sc-urokinase (Ribosepharm GmbH, Haan, Germany) were incubated at 25° C. After 3 min, the reaction was terminated by adding 25 μl of acetic acid (50%) and the absorption was determined at 405 nm using a Microplate Reader (MR 5000, Dynatech, Denkendorf, Germany). The $K_i$ values were determined in accordance with Dixon by means of linear regression using a computer program. The $K_i$ values are the means of at least 3 determinations; the standard deviation was less than 25%.

EXAMPLE 4

In-vitro inhibition of different serine proteases of the trypsin type by Nα-(2,4,6-triisopropylphenyl-sulfonyl)-(L)-3-guanidinophenylalanine-4-ethoxycarbonyl piperazide (uPA inhibitor)

| Enzyme | $K_i$ [μmol/l] uPA Inh. |
|---|---|
| urokinase | 0.47 |
| plasmin | 3.8 |
| thrombin | ≧12 |

The inhibitory effect for the enzymes employed was determined in accordance with the principle described in Example 3.

It is evident from the values given above that the uPA inhibitor according to the invention surprisingly exhibits a smaller $K_i$ value than plasmin by a factor of more than 5 and a $K_i$ value for urokinase which is smaller than that for thrombin by a factor of more than 10. Consequently, the substances according to the invention are suitable for use as selective urokinase inhibitors.

The invention claimed is:

1. A method of treating pancreatic or mammary carcinoma, which comprises administering to a human or animal in need thereof, an effective amount of a compound of formula I

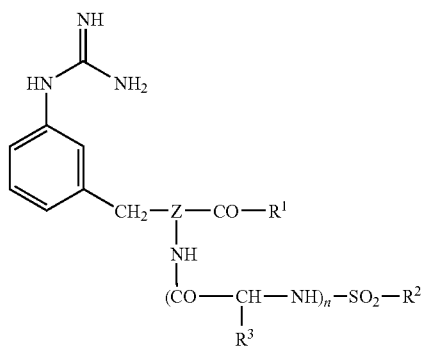
(I)

which are present as racemates or as D- or L-configured compounds and in which R1

(f) is a group of the formula

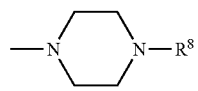

in which $R^8$
(i) is an optionally substituted $C_1$-$C_6$-alkyl radical or aryl radical,
(ii) is a saturated or unsaturated, branched or unbranched $C_1$-$C_6$-alkoxy radical,
(iii) is an optionally substituted oxycarbonyl radical e.g. an ethoxycarbonyl, phenoxycarbonyl or benzyloxycarbonyl radical, or
(iv) is an optionally substituted aminocarbonyl radical, e.g. an ethyl-aminocarbonyl radical,
$R^2$ is an optionally substituted phenyl radical,
$R^3$ is H or branched or unbranched $C_1$-$C_4$-alkyl and n is 0 or 1,
Z is N or $CR^9$, where $R^9$ is H or branched or unbranched $C_1$-$C_4$-alkyl, or pharmaceutically acceptable salts thereof.

2. The method of claim 1, characterized in that $R^1$ is a group of the formulae (b), (d) and (f), $R^2$ is a 2,4,6-triisopropylphenyl radical and n=O.

3. The method of claim 1, characterized in that the compound of the formula I is Nα-(2,4,6-triisopropylphenylsulfonyl)-3-guanidino-(D,L)-phenylalanine-4-ethoxycarbonyl piperazide, Nα-(2, 4, 6-triisopropyl phenylsulfonyl)-3-guanidino-(D,L)-phenylalanine-4-ethylaminocarbonyl piperazide, or the L-enantiomer or a pharmaceutically tolerated salt of one of the compounds.

4. The method of claim 1, characterized in that the compound is present in the form of a physiologically tolerated acid salt.

5. The method of claim 1, characterized in that the compounds of formula I are employed as conjugates with other pharmacologically active substances.

6. The method of claim 1, characterized in that the compounds of formula I are employed in combination with other pharmacologically active substances.

7. The method of claim 5, characterized in that the compounds are employed as conjugates with radiolabels and/or in combination with cytotoxic substances.

8. The method of claim 1, in which the compound is administered orally, topically, rectally or parenterally.

9. The method of claim 1, in which the compound is administered in the form of a tablet, a sugar-coated tablet, a capsule, a pellet, a suppository, a solution or a transdermal system such as a plaster.

10. The method of claim 4, wherein the acid salt is the hydrocholoride salt.

11. A compound of the formula I

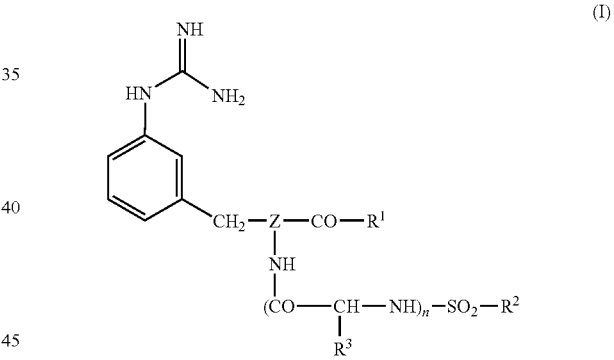
(I)

in which $R^1$, $R^3$, Z and n are defined as in claim 1, and $R^2$ comprises a tri-substituted phenyl radical.

12. Nα-(2, 4, 6-triisopropyl phenylsulfonyl)-3-guanidino-(D, L)-phenylalanine-4-ethoxycarbonyl piperazide, Nα-(2,4, 6-triisopropylphenylsulfonyl)-3-guanidino-(D,L)-phenylalanine-4-ethylaminocarbonyl piperazide or the L-enantiomer thereof, or a pharmaceutically tolerated salt of one of the compounds.

13. A pharmaceutical composition, characterized in that it comprises, as active compound, one or more compounds as claimed in claim 11, where appropriate together with pharmaceutically customary excipients, adjuvants and/or diluents.

14. The compound of claim 11, wherein the substituents on the $R^2$ tri-substituted phenyl radical are independently $C_1$-$C_6$ alkyl, $C_1$-$C_3$ alkoxy, hydroxyl, carboxyl, sulfonyl, nitro, cyano, oxo or halogen.

15. The compound of claim 11, wherein $R^2$ is a 2,4,6-trisubstituted phenyl radical.

* * * * *